United States Patent [19]

Lo

[11] 4,048,994
[45] Sept. 20, 1977

[54] SELF-INFLATING LIQUID CONTAINER FOR KEEPING I.V. FLUID OR BLOOD PLASMA

[76] Inventor: Liu Ying P. Lo, 35-80 Central Ave., Oxford House, Apt. 104, Fort Meyers, Fla. 33901

[21] Appl. No.: 717,116

[22] Filed: Aug. 24, 1976

[51] Int. Cl.² .............................................. A61M 5/00
[52] U.S. Cl. ........................ 128/214 F; 128/DIG. 12; 222/95
[58] Field of Search ........... 128/214 R, 214 F, 214 D, 128/214.2, 225, DIG. 12; 222/94, 95, 386.5

[56] References Cited

U.S. PATENT DOCUMENTS

| 2,409,734 | 10/1946 | Bucher | 128/214 F |
| 2,847,007 | 8/1958 | Fox | 128/214 F |
| 2,876,768 | 3/1959 | Schultz | 128/214 F |
| 3,153,414 | 10/1964 | Beall et al. | 128/DIG. 12 |
| 3,838,794 | 10/1974 | Cogley et al. | 128/214 F X |

FOREIGN PATENT DOCUMENTS 2,310,530  9/1973  Germany ............................ 222/95

Primary Examiner—Dalton L. Truluck
Attorney, Agent, or Firm—Leonard W. Suroff

[57] ABSTRACT

A self-inflating liquid container that includes an inner flexible plastic receptacle for the retention of a liquid such as blood or the like, with a drain tube connected to the lower end of the inner receptacle, so as to permit the outward flow of the liquid from the inner receptacle. Supporting means is connected to the upper end of the inner receptacle so as to permit the liquid contained therein to exit through the drain tube. An outer flexible plastic receptacle substantially surrounds and encloses the inner flexible receptacle so as to form a chamber therebetween, with a first unidirectional valve on the outer receptacle for permitting the inward flow of gas into the chamber such that the outer receptacle can be inflated, so as to obtain a force applied to the inner receptacle to aid in the outward flow of the liquid from the inner receptacle through the drain tube.

4 Claims, 2 Drawing Figures

SELF-INFLATING LIQUID CONTAINER FOR KEEPING I.V. FLUID OR BLOOD PLASMA

BACKGROUND OF THE INVENTION

The present invention relates to a self-inflating liquid container for dispensing and storing intravenous fluid or blood plasma.

In the dispensing of intravenous fluid and blood plasma to a patient, it is desirable to provide an easily utilized container assuring proper fluid of the liquid from the container to the patient. Normally, prior art containers for this purpose rely solely on gravity to obtain the outward flow of the liquid. The inventor of the present invention has found a simple and convenient manner to assist this flow by applying an externally exerted pressure against the receptacle retaining the liquid.

OBJECTS OF THE INVENTION

An object of the present invention is to provide a new and novel self-inflating container for dispensing intravenous fluids and blood plasma.

Another object of the present invention is to provide a liquid container having an inner receptacle for the storage of the fluid therein and an outer receptacle in sealed relationship to the inner receptacle for exerting a force thereagainst to assist the outward flow therefrom.

Other objects and advantages of the present invention will become apparent as the disclosure proceeds.

SUMMARY OF THE INVENTION

A self-inflating liquid container that includes an inner flexible plastic receptacle for the retention of a liquid such as blood or the like, with a drain tube connected to the lower end of the inner receptacle, so as to permit the outward flow of the liquid from the inner receptacle. Supporting means is connected to the upper end of the inner receptacle so as to permit the liquid contained therein to exit through the drain tube. An outer flexible plastic receptacle substantially surrounds and encloses the inner flexible receptacle so as to form a chamber therebetween, with a first unidirectional valve on the outer receptacle for permitting the inward flow of gas into the chamber such that the receptacle can be inflated, so as to obtain a force applied to the inner receptacle to aid in the outward flow of the liquid from the inner receptacle through the drain tube. The supporting means includes a hanger fastened at each end thereof to the inner receptacle and having a portion thereof extending beyond the outer receptacle and in sealed relationship thereto with control means operatively associated with the first valve to control the flow of gas into the chamber. A second valve is also provided to aid in inflating the chamber to apply the compressive force to the inner receptacle to aid in the discharge of the fluid therefrom.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

DETAILED DESCRIPTION OF THE DRAWINGS

Figure 1:
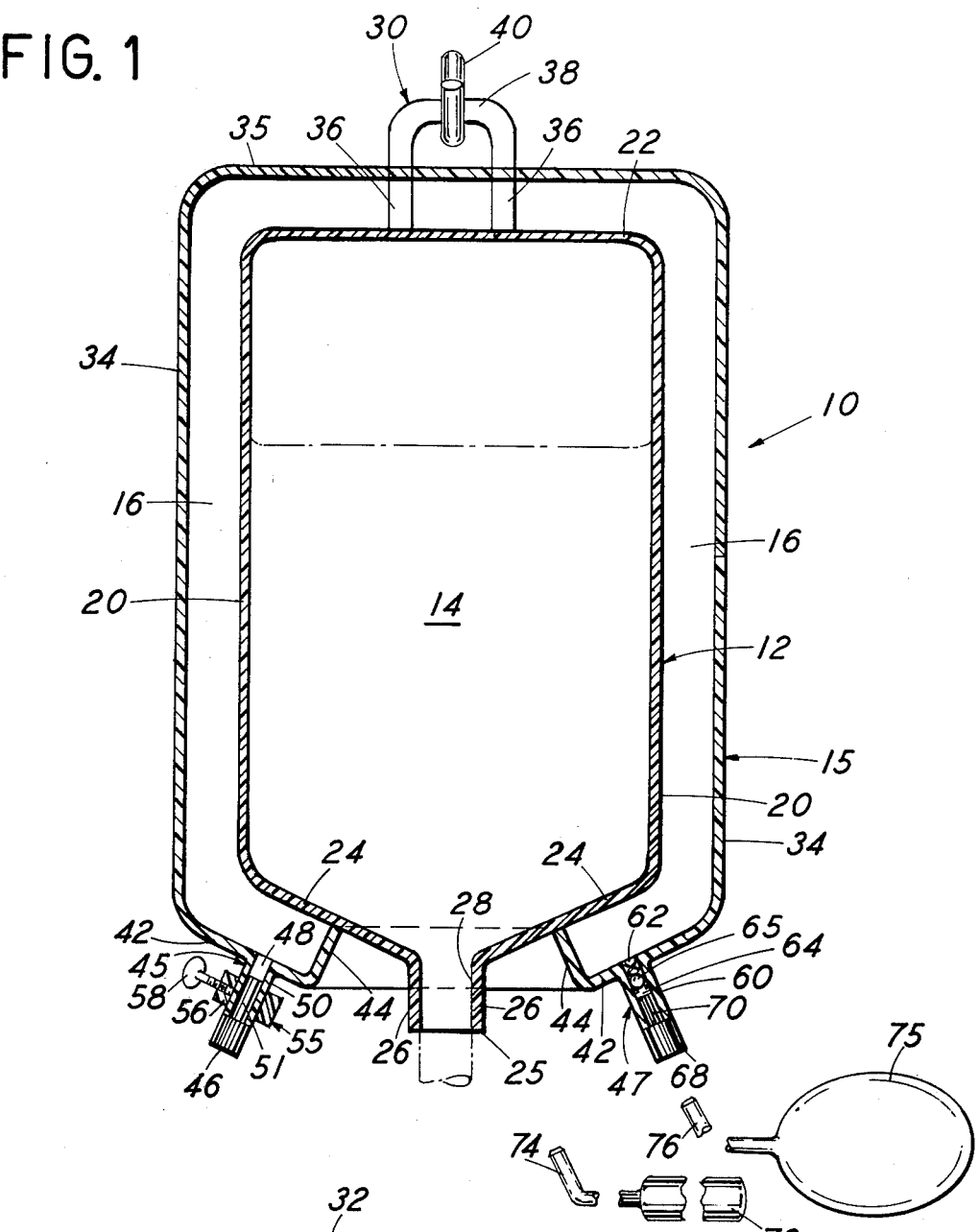
FIG. 1 is a front elevational view, partly in section, of one form of container in accordance with the present invention.
Figure 2:
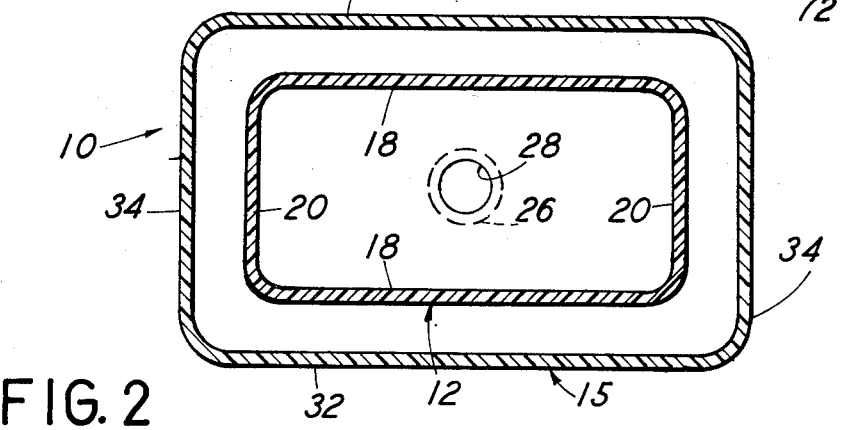
FIG. 2 is a top sectional view of the container illustrated in FIG. 1.

Referring now to FIGS. 1 and 2 of the drawings, there is illustrated a self-inflating liquid container 10 that is formed of an inner flexible plastic receptacle 12 for the retention of a liquid 14 therein. The liquid 14 may be intravenous fluid, blood or the like, that is usually dispensed to patients in hospitals and under other conditions. Associated with the inner receptacle 12 is an outer receptacle 15 made of a plastic flexible material extending substantially in surrounding relationship to and enclosing the inner flexible receptacle 12 so as to form a chamber 16 therebetween.

The inner receptacle 12 includes a pair of inner spaced apart side walls 18 as seen in FIG. 2 and a pair of inner spaced apart end walls 20. An inner top wall 22 joins the inner side walls 18 and inner end walls 20 together. An inner bottom wall 24 is provided in spaced relationship to the inner top wall 22 and similarly joins together the inner side walls 18 and end walls 20. The inner bottom wall 24 is downwardly tapered and communicates in sealed relationship with a drain tube 25 which is connected to the lower end of the inner receptacle 12 so as to permit the outward flow of the liquid 14 therefrom. The drain tube 25 includes a side wall 26 with a vertically extending opening 28 adapted to receive therein the connecting portion of the intravenous system.

During use of the container 10 supporting means 30 is provided at the upper end of the inner receptacle 12 so as to permit the liquid 14 contained therein to exit through the drain tube 25. The outer flexible plastic receptacle 15 includes a pair of spaced apart outer side walls 32 extending in overlapping relationship to the inner side walls 18 and a pair of spaced apart outer end walls 34 extending in overlapping relationship to the inner end walls 20. An outer top wall 35 extends in overlapping relationship to the inner top wall 22 with the supporting means 30 extending through the outer top wall 35. The supporting means 30 may include a pair of spaced apart neck portions 36 firmly secured at one end thereof to the inner top wall 22 and extending through and in sealed relationship to the outer top wall 35. A head portion 38 joins the neck portions 36 such that the hook 40 on the intravenous stand may retain the container 10 in place.

An outer bottom wall 42 extends in partially overlapping relationship to the inner bottom wall 24 and is connected thereto by a peripheral terminal wall portion 44 in surrounding relationship to the outlet tube 25. The material forming the inner receptacle 12 and outer receptacle 15, as well as the associated parts, are made from flexible, plastic materials, preferably transparent. They are designed for sterilized packaging and for ready disposal after a one-time use. The receptacles 12 and 15 are bonded along their perimeters and so constructed to be expanded from a flat collapsed condition into the configuration illustrated. The plastic material forming the container 10 may be heat sealable, elctronically welded, or joined by any other means. The end purpose being that the chamber 16 is gas tight except for a flow of gas that is desired to be introduced therein.

As illustrated in FIG. 1, a pair of valves are provided in operative relationship to the outer receptacle 15. The shape and size of each valve may vary, and for purposes of discussion one valve has been identified as the first unidirectional valve 45 and the other the second unidirectional valve 47. A purpose of the unidirectional valve is essentially to have the gas flowing inwardly into the chamber 16. In accordance with one aspect of the invention, the first unidirectional valve 45 is adapted for permitting the inward flow of gas into the chamber 16 such that the outer receptacle 15 becomes inflated.

By inflating the chamber 16 a force is applied to the inner receptacle 12 to aid in the outward flow of the liquid 14 from the inner receptacle 12 through the drain tube 25. By initially providing 16 in a substantial vacuum, the removal of the plug or cover 46 from valve 45 exposes the valve opening 48 defined by the valve wall 50 that merges with the bottom wall 42. The cover 46 has a shaft 51 that extends axially within the valve opening 48 and may be removed when the supporting means by hanger 38 vertically supports the self-inflating liquid container 10. In this manner when the cover 46 is removed air is sucked into the chamber 16 so that pressure is exerted on the inner receptacle 12 in order to help expel the contents 14 therefrom.

Control means 55 is operatively associated with the first valve 45 to control the flow of gas into the chamber 16. The control means 55 may include a ring 56 surrounding the valve wall 50 with a thumb screw 58 threadably secured to the ring 56 and when turned with the cover 46 removed will vary the size of the opening 48. In this manner when the chamber 16 is initially below atmospheric pressure, it will be inflated by the flow of gas therein to apply a compressor force to the inner receptacle 12.

The second valve 47 has a valve wall 60 with an opening 62 therethrough and a valve seat 64 extending in the opening 62 with a spherical valve member 65 associated therewith. The second valve 47 permits air or any other gas to only flow inwardly into the chamber 16 because of the spherical ball 65 seated against the valve seat 64. A cover 68 having a shaft 70 is utilized with the second valve 47.

The second valve 47 may be used by itself without making use of the first valve 45. Accordingly, if desired, a single valve may even be provided in accordance with the invention. The chamber 16 may be inflated from a source of compressed gas contained in a cartridge 72 having a connecting element 74 adapted to fit within the opening 62. The compressed gas may be supplied from various sources and may be supplied continuously as the level of the liquid 14 decreases so that the pressure in the chamber 16 may be continuously increased to force the liquid 14 out. If desired, the outer receptacle 15 may be manually inflated as by using a blood pressure bulb 75 or the like having a connecting element 76 adapted to be received in the opening 62. Each of the valves may be made from a plastic material and suitable for use for their intended purpose to obtain the necessary inflation of the outer receptacle 15 such that compressive forces are applied to expedite the flow of liquid into the patient in a simple and convenient manner.

Although an illustrative embodiment of the invention has been described in detail herein with reference to the accompanying drawings, it is to be understood that the invention is not limited to the precise embodiment and that various changes and modifications may be effected therein without departing from the scope or spirit of the invention.

I claim:
1. A self-inflating liquid container, comprising:
   a. an inner flexible plastic receptacle for the retention of a liquid such as blood or the like,
   b. a drain tube connected to the lower end of said inner receptacle, so as to permit the outward flow of the liquid from said inner receptacle,
   c. supporting means connected to the upper end of said inner receptacle so as to permit the liquid contained therein to exit through said drain tube,
   d. an outer flexible plastic receptacle substantially surrounding and enclosing said inner flexible receptacle so as to form a chamber therebetween,
   e. a first unidirectional valve on said outer receptacle for permitting the inward flow of gas into said chamber such that said outer receptacle can be inflated, so as to obtain a force applied to said inner receptacle to air in the outward flow of the liquid from said inner receptacle through said drain tube,
   f. said supporting means includes a hanger fastened at one end thereof to said inner receptacle and having a portion thereof extending beyond said outer receptacle and in sealed relationship thereto,
   g. said chamber is initially at or below atmospheric pressure and is inflated by the flow of gas therein to apply a compressive force to said inner receptacle,
   h. a second unidirectional valve on said outer receptacle for permitting the inward flow of gas into said chamber,
   i. said inner receptacle includes:
      1. a pair of inner spaced apart side walls,
      2. a pair of inner spaced apart end walls,
      3. an inner top wall,
      4. an inner bottom wall all joined together with said drain tube extending outwardly therefrom, and
   j. said outer receptacle includes:
      5. a pair of spaced apart outer side walls in overlapping relationship to said inner side walls,
      6. a pair of spaced apart outer end walls in overlapping relationship to said inner end walls,
      7. an outer top wall extending in overlapping relationship to said inner top wall with said supporting means extending through said outer top wall, and
      8. an outer bottom wall extending in partially overlapping relationship to said inner bottom wall and connected thereto by a peripheral terminal wall portion surrounding said outlet tube.

2. A self-inflating liquid container as defined in claim 1, wherein said outer receptacle is inflated from a source of compressed gas.

3. A self-inflating liquid container as defined in claim 1, wherein said outer receptacle includes means permitting manual inflation thereof to be inflated manually.

4. A self-inflating liquid container as defined in claim 1, and further including control means operatively associated with said first valve to control the flow of gas into said chamber.

* * * * *